United States Patent
Zuo et al.

(10) Patent No.: US 9,557,312 B2
(45) Date of Patent: Jan. 31, 2017

(54) DETERMINING PROPERTIES OF OBM FILTRATES

(71) Applicant: Schlumberger Technology Corporation, Sugar Land, TX (US)

(72) Inventors: Youxiang Zuo, Sugar Land, TX (US); Adriaan Gisolf, Houston, TX (US); Li Chen, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 439 days.

(21) Appl. No.: 14/177,744

(22) Filed: Feb. 11, 2014

(65) Prior Publication Data

US 2015/0226059 A1     Aug. 13, 2015

(51) Int. Cl.
  *E21B 49/08*   (2006.01)
  *G01N 33/28*   (2006.01)
  *E21B 41/00*   (2006.01)
  *E21B 49/10*   (2006.01)

(52) U.S. Cl.
  CPC ......... *G01N 33/2835* (2013.01); *E21B 41/005* (2013.01); *E21B 49/10* (2013.01); *G01N 33/2841* (2013.01)

(58) Field of Classification Search
  CPC . G01N 33/2841; G01N 33/2835; E21B 49/10; E21B 40/005; E21B 49/08; E21B 47/12; E21B 23/14
  USPC .......... 702/6, 11, 12, 13; 73/152.42, 152.28; 250/255; 166/250.01, 66
  See application file for complete search history.

(56) References Cited

U.S. PATENT DOCUMENTS

| | | | |
|---|---|---|---|
| 6,729,400 B2 | 5/2004 | Mullins et al. | |
| 6,799,117 B1* | 9/2004 | Proett | E21B 49/08 |
| | | | 702/12 |
| 6,956,204 B2 | 10/2005 | Dong et al. | |
| 7,028,773 B2 | 4/2006 | Fujisawa et al. | |
| 7,081,615 B2* | 7/2006 | Betancourt | E21B 47/10 |
| | | | 250/255 |
| 7,216,533 B2* | 5/2007 | McGregor | E21B 33/1216 |
| | | | 73/152.27 |

(Continued)

OTHER PUBLICATIONS

U.S. Appl. No. 13/865,839, filed Apr. 18, 2013.

(Continued)

*Primary Examiner* — Carol S Tsai
(74) *Attorney, Agent, or Firm* — Trevor G. Grove

(57) ABSTRACT

Methods and apparatus for operating a downhole tool within a wellbore adjacent a subterranean formation to pump contaminated fluid from the formation into the downhole tool while measuring first and second fluid properties of the contaminated fluid. The contaminated fluid comprises native fluid from the formation and a contaminant. The downhole tool is in communication with surface equipment located at surface. The downhole tool and/or surface equipment is operated to estimate a formation volume factor of the contaminated fluid based on at least one of the first and second fluid properties of the contaminated fluid. A linear relationship is then estimated between the first fluid property and a function that relates the first fluid property to the second fluid property and the estimated formation volume factor of the contaminated fluid. A fluid property of the contaminant is then estimated based on the estimated linear relationship.

20 Claims, 8 Drawing Sheets

(56) References Cited

U.S. PATENT DOCUMENTS

| | | | |
|---|---|---|---|
| 7,243,537 B2* | 7/2007 | Proett | E21B 49/08 73/152.51 |
| 7,280,214 B2 | 10/2007 | DiFoggio et al. | |
| 7,526,953 B2* | 5/2009 | Goodwin | E21B 47/10 250/255 |
| 7,920,970 B2* | 4/2011 | Zuo | G01N 33/2823 702/11 |
| 8,024,125 B2 | 9/2011 | Hsu et al. | |
| 8,434,357 B2 | 5/2013 | Hsu et al. | |
| 2004/0104341 A1* | 6/2004 | Betancourt | E21B 47/10 250/255 |
| 2005/0182566 A1 | 8/2005 | DiFoggio | |
| 2006/0226699 A1* | 10/2006 | Betancourt | E21B 47/10 303/113.2 |
| 2007/0119244 A1* | 5/2007 | Goodwin | E21B 47/10 73/152.28 |
| 2007/0175273 A1* | 8/2007 | Follini | E21B 47/10 73/152.27 |
| 2008/0015781 A1* | 1/2008 | Niemeyer | E21B 49/008 702/11 |
| 2011/0088949 A1 | 4/2011 | Zuo et al. | |
| 2011/0284219 A1 | 11/2011 | Pomerantz et al. | |
| 2013/0340518 A1 | 12/2013 | Jones et al. | |
| 2014/0360257 A1* | 12/2014 | Indo | E21B 47/102 73/152.28 |

OTHER PUBLICATIONS

U.S. Appl. No. 14/085,589, filed Nov. 20, 2013.
U.S. Appl. No. 14/085,550, filed Nov. 20, 2013.
U.S. Appl. No. 14/164,991, filed Jan. 27, 2014.
Hsu et al. "Multichannel Oil-Base Mud Contamination Monitoring Using Downhole Optical Spectrometer," SPWLA 49th Annual Logging Symposium, Edinburgh, Scotland, May 25-28, 2008, pp. 1-13.
Kristensen et al. "Flow Modeling and Comparative Analysis for a New Generation of Wireline Formation Tester Modules," IPTC 17385, International Petroleum Technology Conference, Doha, Qatar, Jan. 20-22, 2014, pp. 1-14.
Zuo et al. "A New Method for OBM Decontamination in Downhole Fluid Analysis," IPTC 16524—6th International Petroleum Technology Conference, Beijing, China, Mar. 26-28, 2013.

* cited by examiner

DETERMINING PROPERTIES OF OBM FILTRATES

BACKGROUND OF THE DISCLOSURE

Wellbores (also known as boreholes) are drilled to penetrate subterranean formations for hydrocarbon prospecting and production. During drilling operations, evaluations may be performed of the subterranean formation for various purposes, such as to locate hydrocarbon-producing formations and manage the production of hydrocarbons from these formations. To conduct formation evaluations, the drill string may include one or more drilling tools that test and/or sample the surrounding formation, or the drill string may be removed from the wellbore, and a wireline tool may be deployed into the wellbore to test and/or sample the formation. These drilling tools and wireline tools, as well as other wellbore tools conveyed on coiled tubing, drill pipe, casing or other conveyers, are also referred to herein as "downhole tools."

Formation evaluation may involve drawing fluid from the formation into a downhole tool for testing and/or sampling. Various devices, such as probes and/or packers, may be extended from the downhole tool to isolate a region of the wellbore wall, and thereby establish fluid communication with the subterranean formation surrounding the wellbore. Fluid may then be drawn into the downhole tool using the probe and/or packer. Within the downhole tool, the fluid may be directed to one or more fluid analyzers and sensors that may be employed to detect properties of the fluid while the downhole tool is stationary within the wellbore. Fluid properties like gas-oil ratio (GOR), density, optical density (OD), composition, and others may be measured, detected, and/or estimated utilizing downhole fluid analysis (DFA). These DFA-obtained fluid properties may be utilized for oil-based drilling mud (OBM) filtrate contamination monitoring (OCM).

SUMMARY OF THE DISCLOSURE

The present disclosure introduces a method in which a downhole tool is operated within a wellbore adjacent a subterranean formation to pump contaminated fluid from the subterranean formation into the downhole tool while measuring first and second fluid properties of the contaminated fluid. The contaminated fluid includes native fluid from the subterranean formation and a contaminant. The downhole tool is also in communication with surface equipment located at a wellsite surface associated with the wellbore. At least one of the downhole tool and the surface equipment is operated to estimate a formation volume factor of the contaminated fluid based on at least one of the first and second fluid properties of the contaminated fluid. A linear relationship is then estimated between the first fluid property and a function that relates the first fluid property to the second fluid property and the estimated formation volume factor of the contaminated fluid. A fluid property of the contaminant is then estimated based on the estimated linear relationship.

The present disclosure also introduces a similar method in which at least one of the downhole tool and the surface equipment is operated to determine whether a fluid property of the native fluid can be estimated based on at least one of the first and second fluid properties of the contaminated fluid. If the fluid property of the native fluid can be estimated based on at least one of the first and second fluid properties of the contaminated fluid, at least one of the downhole tool and the surface equipment is operated to estimate the fluid property of the native fluid based on at least one of the first and second fluid properties of the contaminated fluid, and to estimate a linear relationship between the first fluid property and a function comprising the second fluid property, the estimated formation volume factor of the contaminated fluid, and the estimated fluid property of the native fluid. If the fluid property of the native fluid cannot be estimated based on at least one of the first and second fluid properties of the contaminated fluid, at least one of the downhole tool and the surface equipment is operated to estimate a linear relationship between the first fluid property and a function comprising the second fluid property and the estimated formation volume factor of the contaminated fluid.

The present disclosure also introduces a system that includes surface equipment located at a wellsite surface associated with a wellbore extending into a subterranean formation. A downhole tool of the system is operable within the wellbore to communicate with the surface equipment, pump contaminated fluid from the subterranean formation into the downhole tool, and measure first and second fluid properties of the contaminated fluid. The contaminated formation fluid includes native fluid and a contaminant. At least one processor of at least one of the surface equipment and the downhole tool is operable to estimate a formation volume factor of the contaminated fluid based on at least one of the first and second fluid properties of the contaminated fluid. The at least one processor is also operable to estimate a linear relationship between the first fluid property and a function that relates the second fluid property and the estimated formation volume factor of the contaminated fluid. The at least one processor then estimates a fluid property of the contaminant based on the estimated linear relationship.

These and additional aspects of the present disclosure are set forth in the description that follows, and/or may be learned by a person having ordinary skill in the art by reading the materials herein and/or practicing the principles described herein. At least some aspects of the present disclosure may be achieved via means recited in the attached claims.

BRIEF DESCRIPTION OF THE DRAWINGS

The present disclosure may be understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
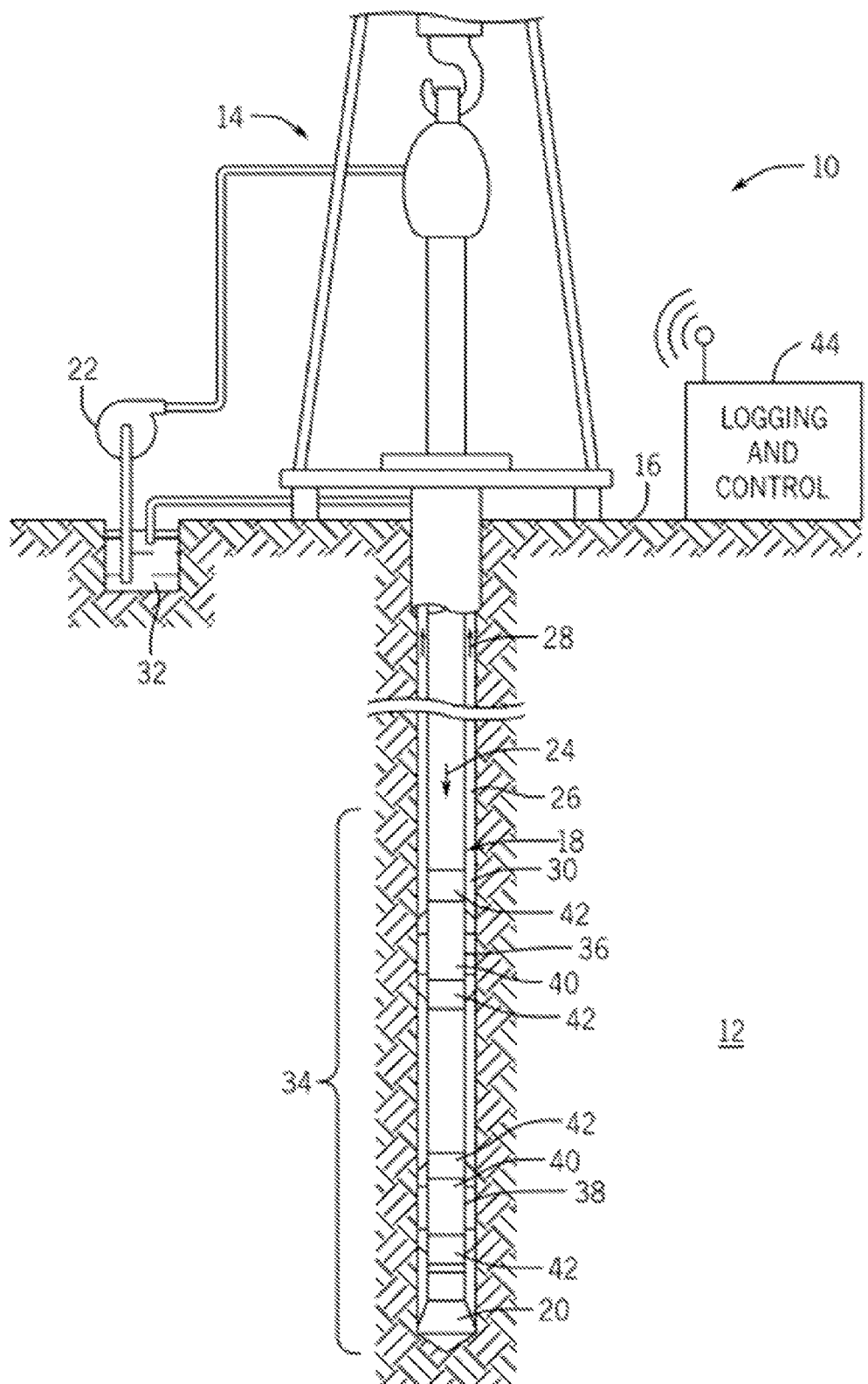
FIG. 1 is a schematic view of at least a portion of apparatus according to one or more aspects of the present disclosure.

It is to be understood that the following disclosure provides many different embodiments, or examples, for implementing different features of various embodiments. Specific examples of components and arrangements are described below to simplify the present disclosure. These are merely examples, of course, and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

One or more aspects of the present disclosure pertain to apparatus and methods for determining properties of OBM filtrates that may be utilized in downhole real-time OBM filtrate contamination monitoring (OCM). The determination may involve estimating various parameters from optical spectra data and combining these parameters according to a particular relationship. The determination may be performed during sampling of the formation fluid, without employing time-consuming pressure/volume/temperature (PVT) analyses on the formation fluid. In certain embodiments, the resulting OBM filtrate properties may be employed to govern sampling operations.

FIG. 1 is a schematic view of at least a portion of a drilling system 10 operable to drill a wellbore 26 through subsurface formations 12. A drilling rig 14 at the wellsite surface 16 is operable to rotate a drill string 18 that includes a drill bit 20 at its lower end. As the drill bit 20 is rotated, a pump 22 pumps drilling fluid (commonly referred to as "mud" or "drilling mud") downward through the center of the drill string 18 in the direction of the arrow 24 to the drill bit 20. The mud, which is utilized to cool and lubricate the drill bit 20, exits the drill string 18 through ports (not shown) in the drill bit 20. The mud then carries drill cuttings away from the bottom of the wellbore 26 as it flows back to the wellsite surface 16 through an annulus 30 between the drill string 18 and the formation 12, as shown by the arrows 28. At the wellsite surface 16, the return mud is filtered and conveyed back to a mud pit 32 for reuse.

While a drill string 18 is illustrated in FIG. 1, it will be understood that the embodiments described herein may be applicable or readily adaptable to work strings and wireline tools as well. Work strings may include a length of tubing (e.g., coiled tubing) lowered into the wellbore 26 for conveying well treatments or well servicing equipment. Wireline tools may include formation testing tools suspended from a multi-conductor cable as the cable is lowered into the wellbore 26 to measure formation properties at desired depths. The location and environment of the drilling system 10 may vary widely depending on the formation 12 penetrated by the wellbore 26. Instead of being a surface operation, for example, the wellbore 26 may be formed under water of varying depths, such as on an ocean bottom surface. Certain components of the drilling system 10 may be specially adapted for underwater wells in such instances.

The lower end of the drill string 18 includes a bottom-hole assembly (BHA) 34, which includes the drill bit 20 and a plurality of drill collars 36, 38. The drill collars 36, 38 may include various instruments, such as sample-while-drilling (SWD) tools that include sensors, telemetry equipment, and so forth. For example, the drill collars 36, 38 may include logging-while-drilling (LWD) modules 40 and/or measurement-while-drilling (MWD) modules 42. The LWD modules or tools 40 may include tools operable to measure formation parameters or properties, such as resistivity, porosity, permeability, sonic velocity, and so forth. The MWD modules or tools 42 may include tools operable to measure wellbore trajectory, borehole temperature, borehole pressure, and so forth. The LWD modules 40 may each be housed in one of the drill collars 36, 38, and may each contain one or more logging tools and/or fluid sampling devices. The LWD modules 40 include capabilities for measuring, processing, and/or storing information, as well as for communicating with the MWD modules 42 and/or directly with the surface equipment such as, for example, a logging and control unit 44. That is, the SWD tools (e.g., LWD and MWD modules 40, 42) may be communicatively coupled to the logging and control unit 44 disposed at the wellsite surface 16. In other implementations, portions of the logging and control unit 44 may be integrated with downhole features.

The LWD modules 40 and/or the MWD modules 42 may include a downhole formation fluid sampling tool operable to selectively sample fluid from the formation(s) 12. The drilling system 10 may be capable of determining certain properties associated with OBM filtrate contaminating sampled formation fluid. These properties may include an estimated density and/or optical density of the OBM filtrate. These and other estimated properties may be determined within or communicated to the logging and control unit 44, such as for subsequent utilization as input to various control functions and/or data logs.

Figure 2:
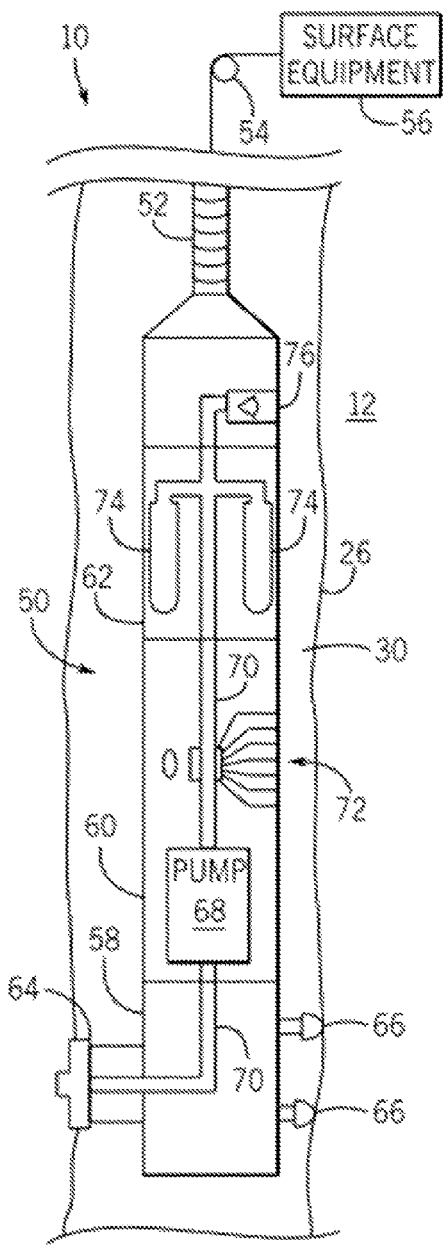
FIG. 2 is a schematic view of at least a portion of apparatus according to one or more aspects of the present disclosure.

FIG. 2 is a schematic diagram of an embodiment of downhole equipment (equipment configured for operation downhole) operable to sample fluid from a formation. The downhole equipment includes an example embodiment of a downhole formation fluid sampling tool 50, hereinafter referred to as the downhole tool 50. The downhole tool 50 is conveyable within the wellbore 26 to the subsurface formation 12 and subsequently operable to sample formation fluid from the formation 12. In the illustrated embodiment, the downhole tool 50 is conveyed in the wellbore 26 via a wireline 52. The downhole tool 50 may be suspended in the wellbore 26 from a lower end of the wireline 52, which may be a multi-conductor cable spooled from a winch 54. The wireline 52 may be electrically coupled to wellsite surface equipment 56, such as to communicate various control signals and logging information between the downhole tool 50 and the wellsite surface equipment 56. The downhole tool 50 may include one or more of the SWD tools depicted in FIG. 1.

The downhole tool 50 includes a probe module 58, a pumpout module 60, and a multi-sample module 62. However, other arrangements and/or modules may make up the downhole tool 50. The probe module 58 may include an extendable fluid communication line (probe 64) operable to engage the formation 12 and communicate fluid samples from the formation 12 into the downhole tool 50. The illustrated probe module 58 may also include one or more setting mechanisms 66. The setting mechanisms 66 may include pistons and/or other apparatus operable to improve fluid communication between the formation 12 and the probe 64. The probe module 58 may also include one or more packer elements (not shown) that inflate or are otherwise operable to contact an inner wall of the wellbore 26, thereby isolating a section of the wellbore 26 for sampling. The probe module 58 may also include electronics, batteries, sensors, and/or hydraulic components used to operate the probe 64 and the corresponding setting mechanisms 66.

The pumpout module 60 may include a pump 68 operable to create a pressure differential that draws the formation fluid in through the probe 64 and pushes the fluid through a flowline 70 of the downhole tool 50. The pump 68 may include an electromechanical, hydraulic, and/or other type of pump operable to pump formation fluid from the probe module 58 to the multi-sample module 62 and/or out of the downhole tool 50. The pump 68 may operate as a piston displacement unit (DU) driven by a ball screw coupled to a gearbox and an electric motor, although other types of pumps 68 are also within the scope of the present disclosure. Power may be supplied to the pump 68 via other components located in the pumpout module 60, or via a separate power generation module (not shown). During a sampling period, the pump 68 moves the formation fluid through the flowline 70 toward the multi-sample module 62.

The pumpout module 60 may also include a spectrometer 72 operable to measure characteristics of the formation fluid as it flows through the flowline 70 toward the multi-sample module 62. The spectrometer 72 may be located downstream or upstream of the pump 68. The characteristics sensed by the spectrometer 72 may include optical density of the formation fluid. Data collected via the spectrometer 72 may be utilized to control the downhole tool 50. For example, the downhole tool 50 may not operate in a sampling mode until the formation fluid flowing through the flowline 70 exhibits characteristics of a clean formation fluid sample, as detected by the spectrometer 72. A clean formation fluid sample contains a relatively low level of contaminants (e.g., drilling mud filtrate) that are miscible with the formation fluid when extracted from the formation.

The multi-sample module 62 includes one or more sample bottles 74 for collecting samples of the formation fluid. Based on the optical density and/or other characteristics of the formation fluid detected via sensors (e.g., the spectrometer 72) along the flowline 70, the downhole tool 50 may be operated in a sampling mode or a continuous pumping mode. When operated in the sampling mode, valves (not shown) disposed at or near entrances of the sample bottles 74 may be positioned to allow the formation fluid to flow into the sample bottles 74. The sample bottles 74 may be filled one at a time, and once a sample bottle 74 is filled, its corresponding valve may be moved to another position to seal the sample bottle 74. When the valves are closed, the downhole tool 50 may operate in a continuous pumping mode.

In the continuous pumping mode, the pump 68 moves the formation fluid into the downhole tool 50 through the probe 64, through the flowline 70, and then out of the downhole tool 50 through an exit port 76. The exit port 76 may be a check valve that releases the formation fluid into the annulus 30 of the wellbore 26. The downhole tool 50 may operate in the continuous pumping mode until the formation fluid flowing through the flowline 70 is determined to be clean enough for sampling. That is, when the formation fluid is first sampled, drilling mud filtrate that has been forced into the formation via the drilling operations may enter the downhole tool 50 along with the sampled formation fluid. After pumping the formation fluid for an amount of time, the formation fluid flowing through the downhole tool 50 will provide a cleaner fluid sample of the formation 12 than would otherwise be available when first drawing fluid in through the probe 64. The formation fluid may be considered clean when the optical spectra data from the spectrometer 72 indicates that the formation fluid contains less than approximately 1%, 5%, or 10% filtrate contamination (by volume).

Figure 3:
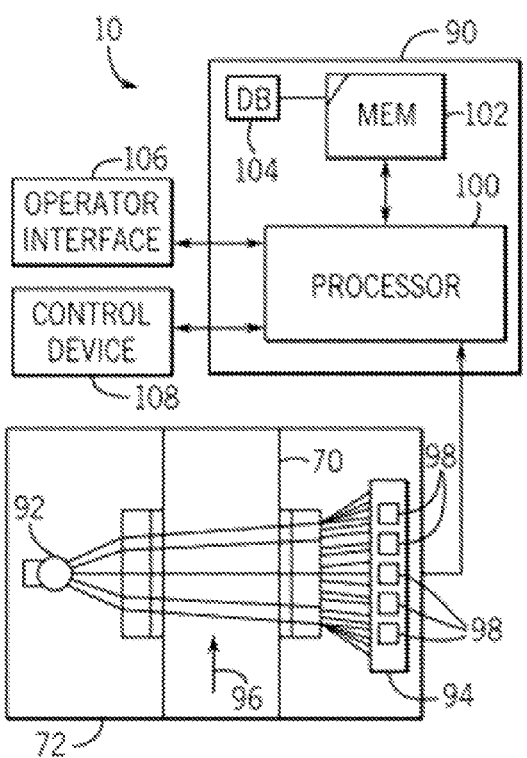
FIG. 3 is a schematic view of at least a portion of apparatus according to one or more aspects of the present disclosure.

The characteristics of the formation fluid measured by the spectrometer 72 may be useful for performing a variety of evaluation and control functions, in addition to determining when the formation fluid flowing through the flowline 70 is clean enough for sampling. For example, data may be collected from the spectrometer 72 and/or other sensors within the downhole tool, such as a density sensor, a viscosity sensor, and/or a saturation pressure sensor, among others. The collected data may be utilized to estimate a formation volume factor of the contaminated formation fluid, as well as density, optical density, GOR, compressibility, saturation pressure, viscosity, and/or mass fractions of compositional components of the contaminated formation fluid and/or contaminants therein (e.g., OBM filtrate), among others. FIG. 3 is a schematic diagram of the spectrometer 72 and a control/monitoring system 90 may be utilized in the drilling system 10 to estimate or determine such properties.

The spectrometer 72 may include a light source 92 and a detector 94 disposed on opposite sides of the flowline 70 through which the formation fluid flows, as indicated by arrow 96. The spectrometer 72 may be part of the downhole tool 50, and may be located at various possible locations along the flowline 70 that directs the formation fluid through the downhole tool 50. Although a single light source 92 is shown in the example depicted in FIG. 3, the spectrometer 72 may include additional light sources 92. The detector 94 may sense the light that passes through the formation fluid in the flowline 70.

The detector 94 may include one or more detector elements 98 that may each be operable to measure the amount of light transmitted at a certain wavelength. For example, the detector elements 98 may detect the light transmitted from the visible to near-infrared within a range of 1, 5, 10, 20, or more different wavelengths ranging between about 400 nm and about 2200 nm. However, other numbers of wavelengths (corresponding to the number of detector elements) and other ranges of wavelengths are also within the scope of the present disclosure. For example, optical characteristics of the formation fluid may be detected at a relatively limited range of wavelengths, such as the near infrared (NIR)

wavelength range of approximately 800-2500 nm, 1500-2050 nm, or 1600-1800 nm. Estimations of formation fluid properties according to one or more aspects of the present disclosure may utilize optical data collected at a single wavelength or at multiple wavelengths.

The spectrometer 72 may measure one or more optical characteristics of the formation fluid flowing through the flowline 70 and output optical spectra and/or other data representative of the detected optical characteristics. The optical characteristics may include optical density of the formation fluid at each of the detected wavelengths. Optical density is a logarithmic measurement relating the intensity of light emitted from the light source 92 to the intensity of light detected by the detector 94 at a certain wavelength.

The spectrometer 72 may send optical spectra and/or other data representative of the measured optical characteristics to a processor 100 of the control/monitoring system 90. In the context of the present disclosure, the term "processor" refers to any number of processor components located about the drilling system 10. The processor 100 may include a single processor disposed onboard the downhole tool 50. In other implementations, at least a portion of the processor 100 (e.g., multiple processors collectively operating as the processor 100) may be located within the wellsite surface equipment 56 of FIG. 2, the logging and control unit 44 of FIG. 1, and/or other surface equipment components. The processor 100 may also or instead be or include one or more processors located within the downhole tool 50 connected to one or more processors located in drilling equipment disposed at the wellsite surface 16. Moreover, various combinations of processors may be considered part of the processor 100 in the following discussion. Similar terminology is applied with respect to the control/monitoring system 90 as well as a memory 102 of the control/monitoring system 90, meaning that the control/monitoring system 90 may include various processors communicatively coupled to each other and/or to memories located throughout the drilling system 10.

The control/monitoring system 90 may estimate the formation volume factor of the contaminated fluid based on the optical spectra data received from the spectrometer 72, a density sensor, and/or other sensors, and may utilize the estimated formation volume factor of the contaminated fluid to determine density, optical density, GOR, mass fractions of compositional components, and/or other properties of the formation fluid, the contaminated fluid, and/or contaminants therein. To make these and other calculations, the processor 100 may execute instructions stored in the memory 102.

The processor 100 may utilize one or more datasets stored in a database 104 within the memory 102. Such datasets may include a record of optical spectra data and corresponding parameters (e.g., composition, formation volume factor, de-colored optical spectrum) of the formation fluid taken via prior formation fluid sampling using the downhole tool 50. The formation fluid parameters stored in the dataset may include results from laboratory tests performed on formation fluid previously sampled by the downhole tool 50. In some embodiments, the processor 100 may use information derived from the dataset to estimate the formation volume factor based on expected results for the optical spectra data from prior formation fluid samples in the database. As more samples are taken using the downhole tool 50, the datasets may be updated within the database 104 to include more information for performing the estimations.

The processor 100 may be communicatively coupled with one or more operator interfaces 106 and/or control devices 108. The operator interface 106 may include logs of predicted formation fluid properties that are accessible to an operator. The control device 108 may include one or more devices and/or portions of the drilling system 10 that receive control signals for operation based on the estimated properties of the formation fluid. Such control devices 108 may implement changes in depth of the downhole tool 50 within the wellbore 26, adjustments to the pumping pressure of the pump 68, and/or other control functions, based on the estimated formation fluid properties.

The volume fraction of the OBM filtrate contamination of contaminated fluid sampled from a formation ($v_{obm}$) can be expressed in different ways, based on the type of sensor utilized to obtain measurements of the contaminated fluid. For example, where an optical sensor is utilized, such as the spectrometer 72 described above, the volume fraction of the OBM filtrate contamination of the contaminated fluid ($v_{obm}$) can be expressed as set forth below in Equation (1):

$$v_{obm} = \frac{OD_{native:i} - OD_{contaminated:i}}{OD_{native:i} - OD_{obm:i}} \qquad (1)$$

where $OD_{native:i}$ is the optical density of the native, uncontaminated fluid at channel i of the multi-channel sensor utilized to measure, estimate, or otherwise obtain optical density of the native fluid, $OD_{contaminated:i}$ is the optical density of the contaminated fluid (also referred to as apparent optical density) at channel i, and $OD_{obm:i}$ is the optical density of the OBM filtrate at channel i.

When a density sensor is utilized, the volume fraction of the OBM filtrate contamination of the contaminated fluid ($v_{obm}$) can be expressed as set forth below in Equation (2):

$$v_{obm} = \frac{\rho_{native} - \rho_{contaminated}}{\rho_{native} - \rho_{obm}} \qquad (2)$$

where $\rho_{native}$ is the density of the native, uncontaminated fluid, $\rho_{contaminated}$ is the density of the contaminated fluid (also referred to as apparent density, which may be measured by DFA), and $\rho_{obm}$ is the optical density of the OBM filtrate.

When a GOR sensor is utilized, the volume fraction of the OBM filtrate contamination of the contaminated fluid ($v_{obm}$) can be expressed as set forth below in Equation (3):

$$v_{obm} = b \frac{GOR_{native} - GOR_{contaminated}}{GOR_{native}}, \qquad (3)$$

$$b = \frac{B_{obm}}{B_{contaminated}}$$

where $GOR_{native}$ is the GOR of the native, uncontaminated fluid, $GOR_{contaminated}$ is the GOR of the contaminated fluid (also referred to as apparent GOR, which may be measured by DFA), $B_{obm}$ is the formation volume factor of the OBM filtrate, and $B_{contaminated}$ is the formation volume factor of the contaminated fluid.

The volume fraction of the OBM filtrate contamination of the contaminated fluid at standard (e.g., stock tank) conditions ($v_{obm-std}$) can be converted to the volume fraction of the OBM filtrate contamination of the contaminated fluid at reservoir conditions ($v_{obm}$) by the shrinkage factor b given in Equation (3). The formation volume factor of the contaminated fluid ($B_{contaminated}$) is defined as the ratio of the volume at reservoir conditions ($V_{contaminated-res}$) to the volume at standard conditions ($V_{contaminated\text{-}std}$), and may be expressed as set forth below in Equation (4):

$$B_{contaminated} = \frac{V_{contaminated-res}}{V_{contaminated-std}} \quad (4)$$

$$= \left(\frac{\rho_{contaminated-std}}{\rho_{contaminated}}\right)\left(1 + \frac{GOR_{contaminated}}{\rho_{contaminated-std}} \frac{M_{gas}P_{std}}{RT_{std}}\right)$$

$$= \left(\frac{\rho_{contaminated-std}}{\rho_{contaminated}}\right)\left(1 + \frac{GOR_{contaminated}M_{gas}}{23.69\rho_{contaminated-std}}\right)$$

where $\rho_{contaminated\text{-}std}$ is the density of the contaminated fluid at standard conditions and $M_{gas}$ is the gas molecular weight at standard conditions. $P_{std}$ and $T_{std}$ are the pressure and temperature, respectively, of standard conditions (e.g., 14.7 psi and 60° F.), and R is the gas constant (23.69 when based on SI units). The apparent GOR ($GOR_{contaminated}$) and apparent density ($\rho_{contaminated}$) may be measured by DFA and/or other means. The gas molecular weight ($M_{gas}$) may be determined utilizing similar DFA measurements and/or other means. The density of the contaminated fluid at standard conditions ($\rho_{contaminated\text{-}std}$) may be estimated via utilization of an artificial neural network (ANN) and/or other means that may be utilized in DFA/GOR algorithms.

The formation volume factor of the OBM filtrate ($v_{obm}$) is defined as the ratio of the volume at reservoir conditions ($V_{obm\text{-}res}$) to the volume at standard conditions ($V_{obm\text{-}std}$), and may be expressed as set forth below in Equation (5):

$$B_{obm} = \frac{V_{obm-res}}{V_{obm-std}} \quad (5)$$

$$= \frac{\rho_{obm-std}}{\rho_{obm-res}}$$

where $\rho_{obm\text{-}std}$ is the density of the OBM filtrate at standard conditions and $\rho_{obm\text{-}res}$ is the density of the OBM filtrate at standard conditions. The formation volume factor of the OBM filtrate ($B_{obm}$) may be approximately equal to 1, such that the shrinkage factor b may be about equal to $1/B_{contaminated}$.

Equations (1), (2), and (3) may be equalized as set forth below in Equation (6):

$$v_{obm} = \frac{OD_{native:i} - OD_{contaminated:i}}{OD_{native:i} - OD_{obm:i}} \quad (6)$$

$$= \frac{\rho_{native} - \rho_{contaminated}}{\rho_{native} - \rho_{obm}}$$

$$= b\frac{GOR_{native} - GOR_{contaminated}}{GOR_{native}}$$

The formation volume factor of the contaminated fluid ($B_{contaminated}$) is linearly related to the GOR of the contaminated fluid ($GOR_{contaminated}$) when the OBM filtrate is added to the uncontaminated fluid. This linear relationship is set forth below in Equation (7):

$$B_{contaminated} = 1 + c(GOR_{contaminated}) \quad (7)$$

where c is a constant of the linear relationship, which experiments have revealed to range between about $3.64 \times 10^{-4}$ and about $4.31 \times 10^{-4}$.

For low GOR fluids (e.g., less than about 700 scf/bbl), the formation volume factor of the native fluid ($B_{native}$) is close to 1. Therefore, linear relationships of OD and density relative to the GOR of the contaminated fluid ($GOR_{contaminated}$) can be utilized to determine the OD and density of the OBM filtrate by extrapolation and zeroing the GOR of the contaminated fluid ($GOR_{contaminated}$).

Figure 4:
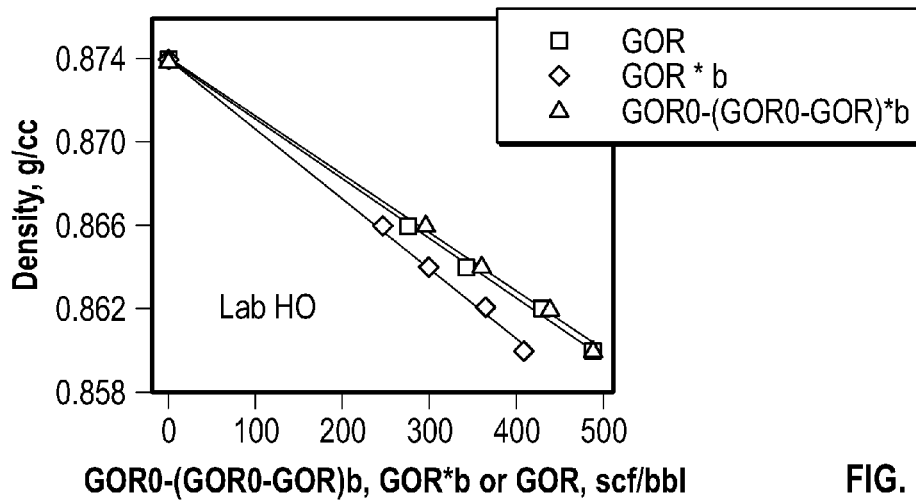
FIG. 4 is a graph depicting one or more aspects of the present disclosure.
Figure 5:
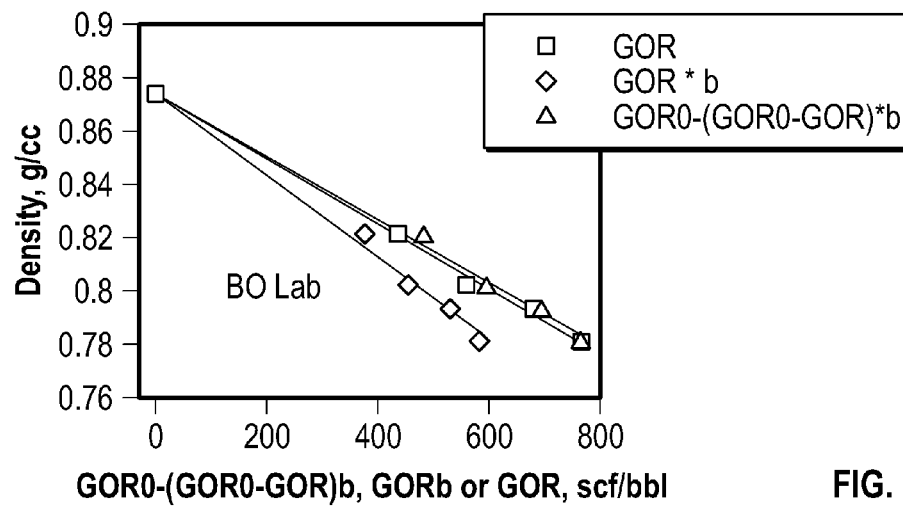
FIG. 5 is a graph depicting one or more aspects of the present disclosure.
Figure 6:
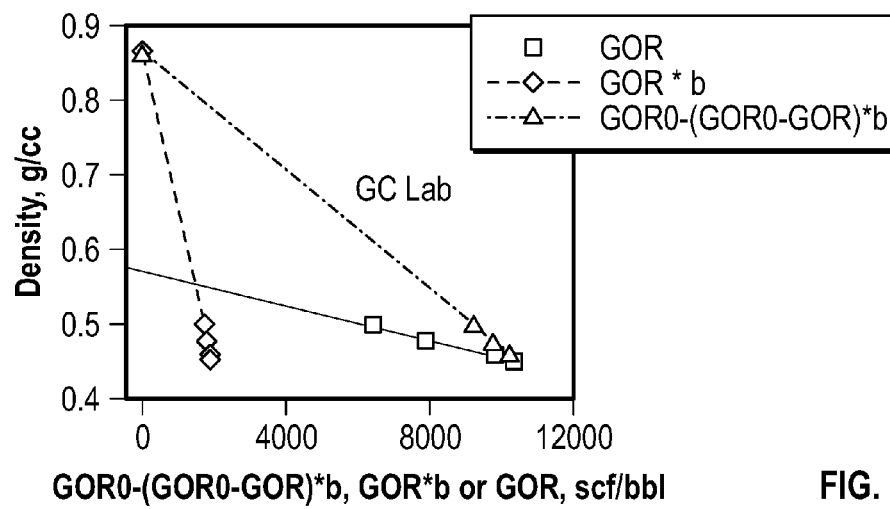
FIG. 6 is a graph depicting one or more aspects of the present disclosure.

FIGS. 4-6 depict lab data of density vs. GOR for an example heavy oil (HO), an example black oil (BO), and an example gas condensate (GC), respectively. As shown in FIGS. 4 and 5, when a linear relationship exists between density and GOR for heavy oil and black oil, which may have a GOR that is less than about 700 scf/bbl, the relationship can be extrapolated (e.g., to GOR=0) to estimate with reasonable accuracy the density of the OBM filtrate that is mixed with the heavy oil and black oil. However, for gas condensate, which may have a GOR that is greater than about 700 scf/bbl, a similar extrapolation may yield inaccurate results. For example, in FIG. 6, the lab-determined density of the OBM filtrate is about 0.87 g/cc, while the extrapolated density is about 0.67 g/cc, which is inaccurate by more than about 20%. Such inaccuracies may also exist for volatile oils having a GOR that is greater than about 700 scf/bbl. Moreover, similar results are obtained for OD vs. GOR. That is, discrepancies exist between actual OD and the OD extrapolated to zero-GOR based on a plot of OD vs. GOR.

The cause of these discrepancies for high GOR fluids may be revealed by substituting Equation (7) into Equation (6), as set forth below in Equation (8):

$$v_{obm} = \frac{OD_{native:i} - OD_{contaminated:i}}{OD_{native:i} - OD_{obm:i}} \quad (8)$$

$$= \frac{\rho_{native} - \rho_{contaminated}}{\rho_{native} - \rho_{obm}}$$

$$= b\frac{GOR_{native} - GOR_{contaminated}}{GOR_{native}}$$

$$\approx \frac{(GOR_{native} - GOR_{contaminated})}{GOR_{native}(1 + c(GOR_{contaminated}))}$$

That is, for low GOR fluids, ignoring $c(GOR_{contaminated})$ may not result in a significant error. Therefore, one can extrapolate the linear relationship between density and GOR to zero-GOR to obtain the OBM filtrate properties. However, this may not be done to obtain OBM filtrate properties for high GOR fluids, because density and optical density are non-linearly related to GOR in the full GOR spectrum, ranging from the OBM filtrate to the native fluid.

Therefore, from Equation (8), if the optical density and GOR of the contaminated fluid ($OD_{contaminated}$ and $GOR_{contaminated}$) are measured by the downhole tool, then the density and optical density of the OBM filtrate ($\rho_{obm}$ and $OD_{obm}$) can be estimated according to one or more aspects introduced herein. Additional known or future-developed methods may be utilized to determine fluid properties of the native fluid, such that the measured data, the native fluid properties, and the OBM filtrate properties can be utilized to estimate OCM.

However, according to Equation (7), when $GOR_{contaminated}$ is equal to 0, the formation volume factor of the contaminated fluid ($1/B_{contaminated}$) will be equal to 1. Consequently, according to Equation (3), the shrinkage factor b ($1/B_{contaminated}$) will also be equal to 1, and the expression [$b(GOR_{native} - GOR_{contaminated})$] will also be equal to $GOR_{native}$. Thus, to determine the OBM filtrate properties graphically, the expression [b(GOR$_{native}$−GOR$_{contaminated}$)] may be replaced by an auxiliary expression $f$ set forth below in Equation (9):

$$f = GOR_{native} - b(GOR_{native} - GOR_{contaminated}) \quad (9)$$

Figure 7:
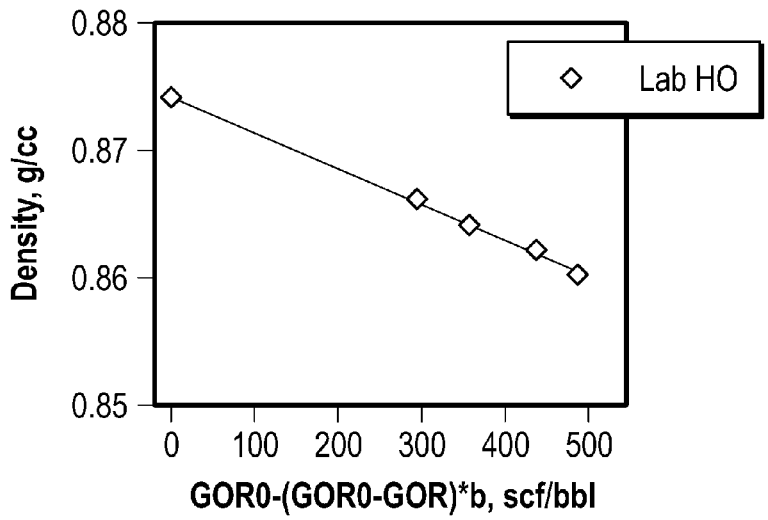
FIG. 7 is a graph depicting one or more aspects of the present disclosure.
Figure 8:
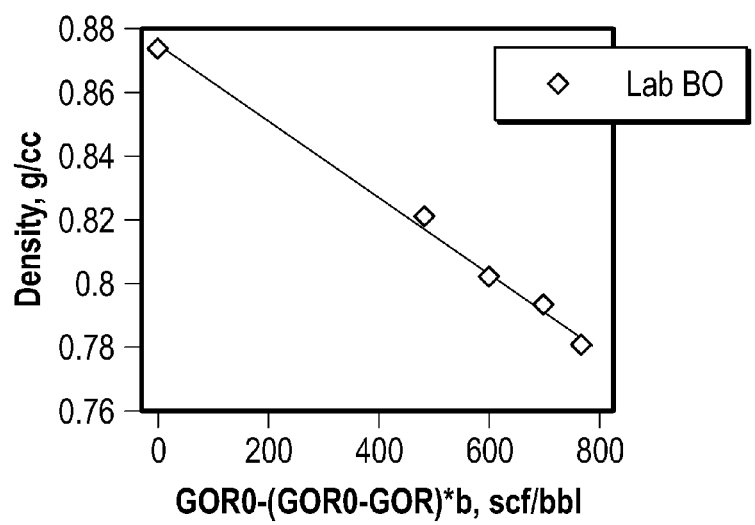
FIG. 8 is a graph depicting one or more aspects of the present disclosure.
Figure 9:
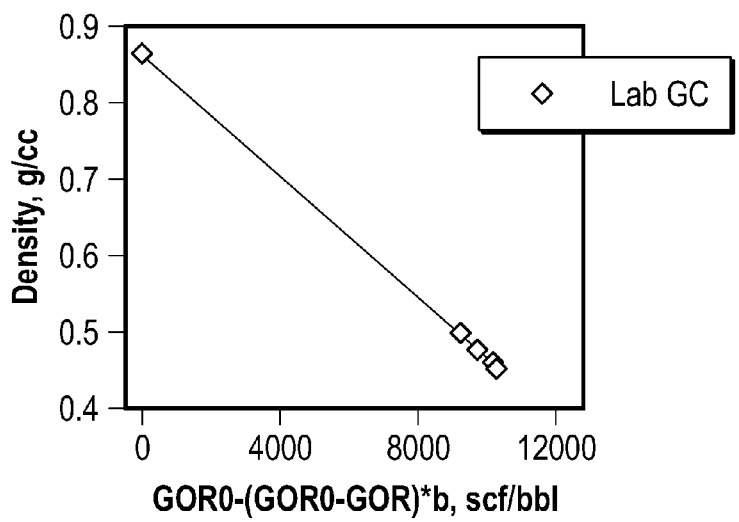
FIG. 9 is a graph depicting one or more aspects of the present disclosure.

Setting the auxiliary expression $f$ equal to one of the measurements obtained by DFA (e.g., $\rho_{contaminated}$ or OD$_{contaminated}$) provides a substantially linear relationship from which one or more properties of the OBM filtrate may be estimated or otherwise obtained. For example, FIGS. 7-9 graphically depict the substantially linear relationship between lab-obtained density and the auxiliary function $f$ for an example heavy oil (HO), an example black oil (BO), and an example gas condensate (GC), respectively. The substantially linear relations can be observed over the entire range of GOR values in each of FIGS. 7-9.

Formation testing operations may provide datasets that contain OD, density, and GOR data at a range of contaminations, but the datasets do not cover the pure filtrate at 100% contamination. Nonetheless, since the GOR of the OBM filtrate (GOR$_{obm}$) is equal to zero, the substantially linear relationship of the expression $f$ to the OD or density of the contaminated fluid may be utilized to estimate the OD or density of the OBM filtrate by extrapolating the relationship to where the expression $f$ is equal to 0.

Experimentation has revealed that determining the substantially linear relationship between OD or density of the contaminated fluid to the expression $f$ can provide an acceptably accurate estimate of the OD or density of the OBM filtrate in the contaminated fluid, which can then be utilized to monitor the contamination level of the contaminated fluid relative to, for example, pumpout time and/or volume. However, the expression $f$ includes the GOR of the native fluid (GOR$_{native}$), which is not always obtainable from the available DFA measurements. Nonetheless, experimentation has also revealed similar results for the linear relationship between OD or density of the contaminated fluid and the apparent GOR of the contaminated fluid corrected by the shrinkage factor b, which is the inverse of the formation volume factor of the contaminated fluid (B$_{contaminated}$), as set forth below in Equation (10) as the expression g:

$$g = (GOR_{contaminated})/B_{contaminated} = b(GOR_{contaminated}) \quad (10)$$

Figure 10:
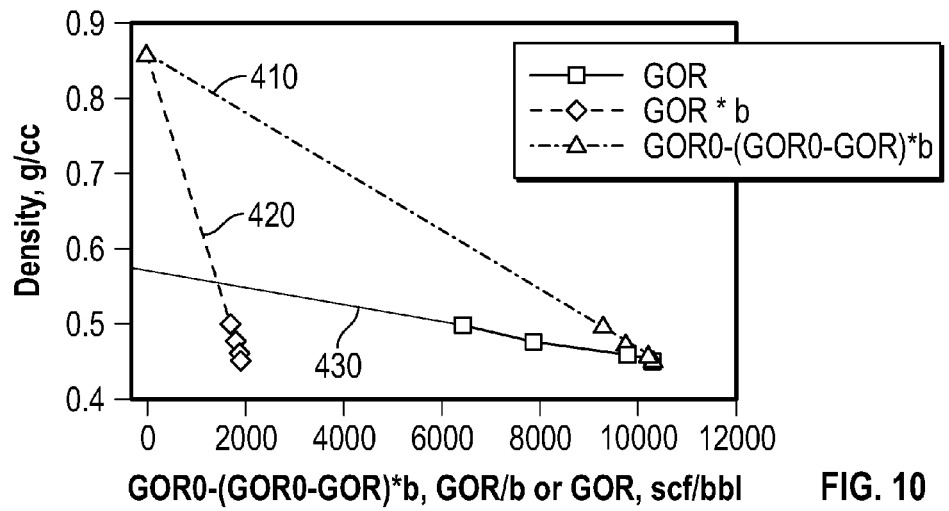
FIG. 10 is a graph depicting one or more aspects of the present disclosure.
Figure 11:
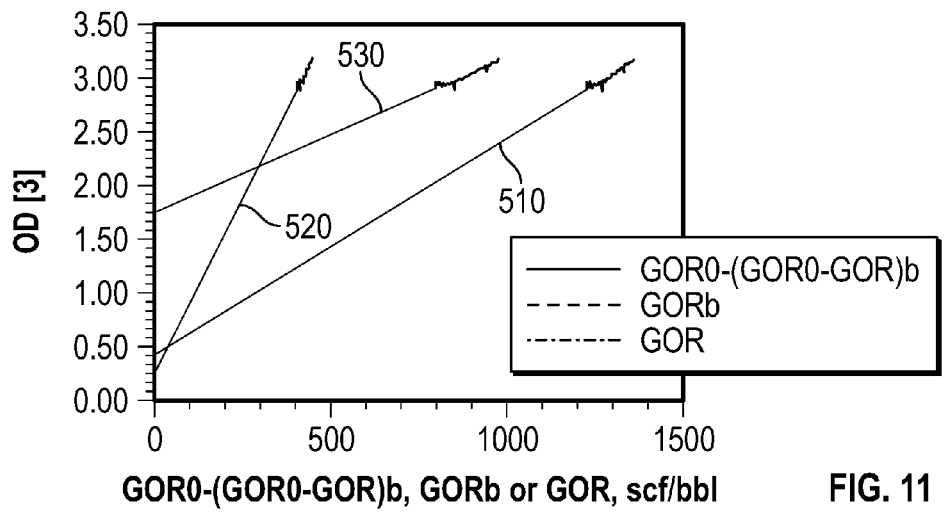
FIG. 11 is a graph depicting one or more aspects of the present disclosure.
Figure 12:
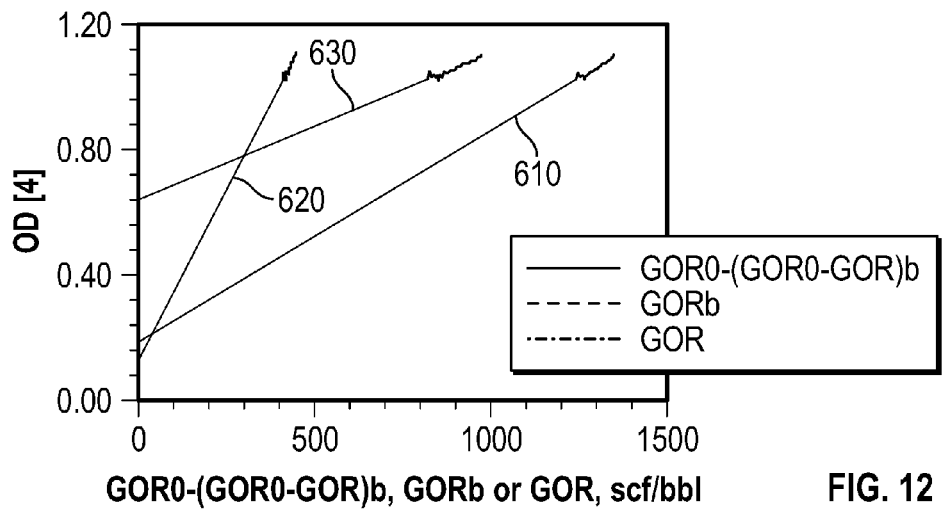
FIG. 12 is a graph depicting one or more aspects of the present disclosure.
Figure 13:
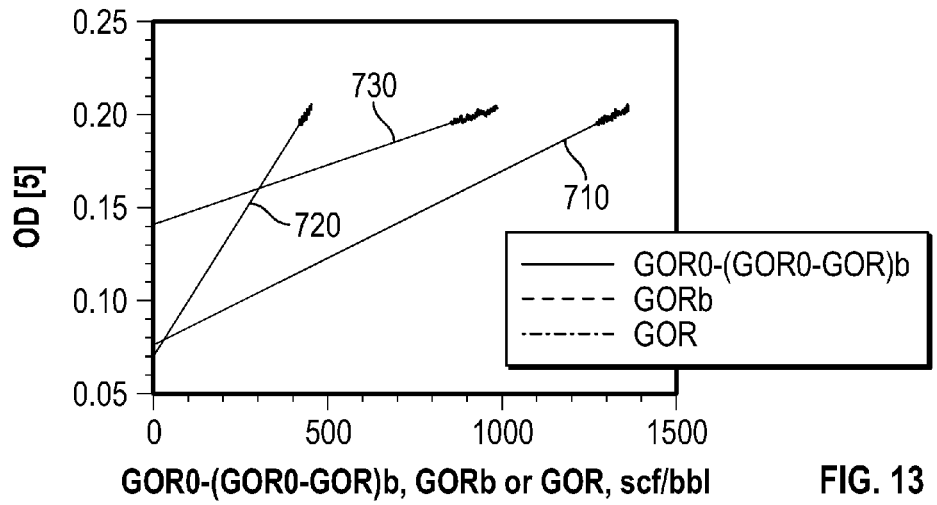
FIG. 13 is a graph depicting one or more aspects of the present disclosure.
Figure 14:
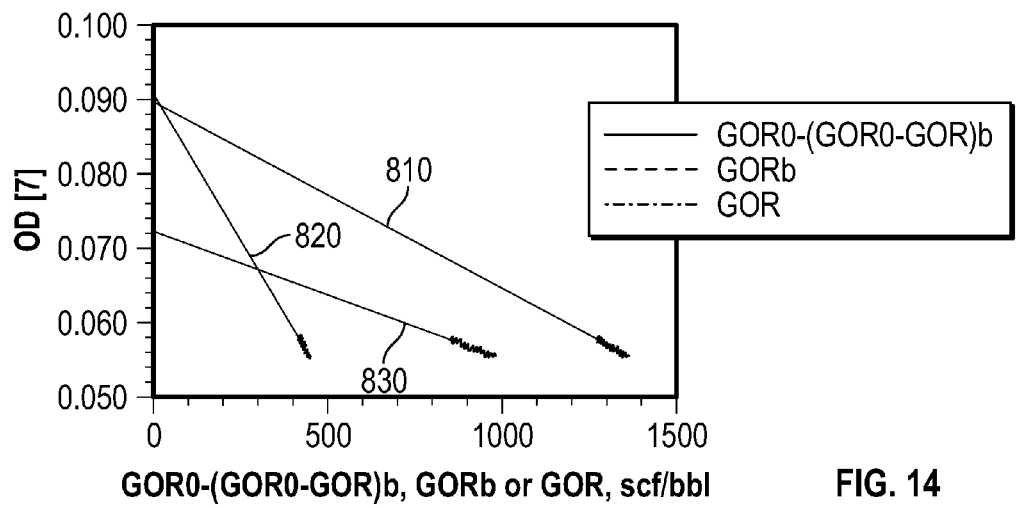
FIG. 14 is a graph depicting one or more aspects of the present disclosure.

Experimentation has revealed that, when the GOR of the native fluid (GOR$_{native}$) is available, the expression $f$ in Equation (9) is a more accurate tool for determining the density or OD of the OBM filtrate, relative to the expression g in Equation (10). However, the experimentation also reveals that, when the GOR of the native fluid (GOR$_{native}$) is not available, the results obtained utilizing the expression g in Equation (10) can provide nearly similar accuracy. This is demonstrated in FIG. 10, in which a first curve 410 depicts the relationship between density of the contaminated fluid ($\rho_{contaminated}$) and the expression $f$ in Equation (9), a second curve 420 depicts the relationship between density of the contaminated fluid ($\rho_{contaminated}$) and the expression g in Equation (10), and a third curve 430 depicts the relationship between density of the contaminated fluid ($\rho_{contaminated}$) and the GOR of the contaminated fluid (GOR$_{contaminated}$). As shown in FIG. 10, the first and second curves 410 and 420 each extrapolate to an OBM filtrate density of about 0.86 g/cc, while the third curve 430 extrapolates to about 0.57 g/cc, representing an error of greater than about 33%.

FIGS. 11-14 are graphs illustrating similar relationships with respect to OD at four different channels of a downhole spectrometer and/or other optical sensor. In FIGS. 11-14, curves 510, 610, 710, and 810 each depict the relationship between optical density of the contaminated fluid ($\rho_{contaminated}$) at a corresponding one of the four channels and the expression $f$ in Equation (9), curves 520, 620, 720, and 820 each depict the relationship between density of the contaminated fluid ($\rho_{contaminated}$) at the corresponding channel and the expression g in Equation (10), and curves 530, 630, 730, and 830 each depict the relationship between density of the contaminated fluid ($\rho_{contaminated}$) at the corresponding channel and the GOR of the contaminated fluid (GOR$_{contaminated}$). As shown in FIGS. 11-14, the curves 510, 610, 710, and 810 each extrapolate to an OBM filtrate optical density that is similar to the extrapolation of the curves 520, 620, 720, and 820, respectively, while the curves 530, 630, 730, and 830 each incorrectly extrapolate to a substantially different OBM filtrate optical density. Moreover, combining the results of doing this for each optical channel can be utilized to construct the spectrum of the OBM filtrate.

Figure 15:
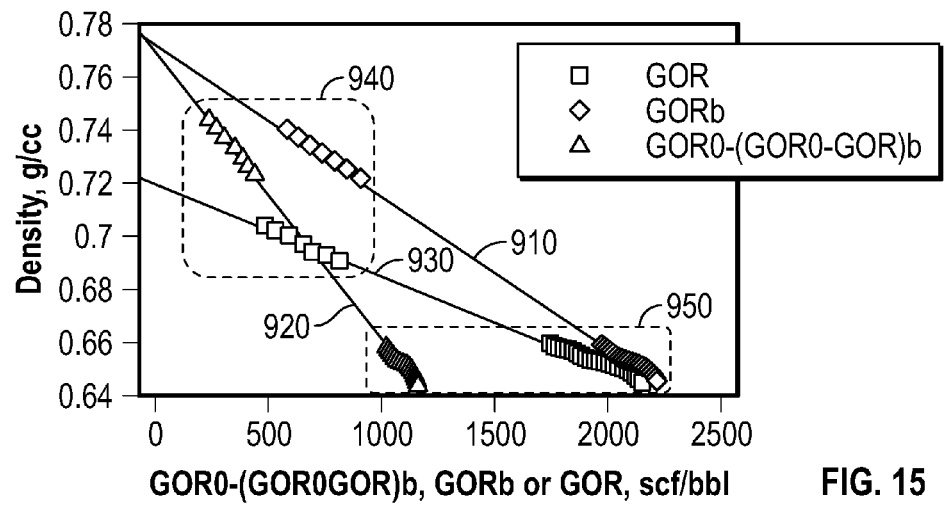
FIG. 15 is a graph depicting one or more aspects of the present disclosure.

One or more aspects of the present disclosure may also be applicable or readily adaptable to focused sampling, in which the sampling probe (e.g., the probe 64 shown in FIG. 2) includes a sample inlet and a guard inlet surrounding the sample inlet. The sample and guard inlets may each lead to separate flowlines within the downhole tool. However, because the guard inlet surrounds the sample inlet, the flowline from the sample inlet may have much less OBM filtrate contamination relative to the flowline from the guard inlet. Accordingly, the contaminated fluid flowing through the sample flowline may have a substantially larger GOR than the contaminated fluid flowing through the guard flowline. Therefore, more robust linear relationships and extrapolation may be obtained via plots of density or OD vs. the expression $f$ in Equation (9) and/or the expression g in Equation (10) by utilizing data from both flowlines (combining the flow from the sample and guard inlets). One example of this potential benefit is depicted in FIG. 15, in which a first curve 910 depicts the relationship between density of the contaminated fluid ($\rho_{contaminated}$) and the expression $f$ in Equation (9), a second curve 920 depicts the relationship between density of the contaminated fluid ($\rho_{contaminated}$) and the expression g in Equation (10), and a third curve 930 depicts the relationship between density of the contaminated fluid ($\rho_{contaminated}$) and the GOR of the contaminated fluid (GOR$_{contaminated}$). In FIG. 15, the higher-density data points 940 correspond to data obtained from contaminated fluid flowing in the guard line, whereas the lower-density data points 950 correspond to data obtained from contaminated fluid flowing in the sample line.

To obtain the expression $f$ of Equation (9), the GOR, density, optical density, and mass fraction may be fitted utilizing the power functions set forth below in Equations (11)-(14):

$$GOR_{contaminated} = GOR_{native} - \beta_1(V_{pumpout})^{-\gamma} \quad (11)$$

$$\rho_{contaminated} = \rho_{native} - \beta_2(V_{pumpout})^{-\gamma} \quad (12)$$

$$OD_{contaminated:i} = OD_{native:i} - \beta_3(V_{pumpout})^{-\gamma} \quad (13)$$

$$m_{contaminated:j} = m_{native:j} - \beta_4(V_{pumpout})^{-\gamma} \quad (14)$$

where $\beta_1$, $\beta_2$, $\beta_3$, $\beta_4$, and $\gamma$ are variables determined via regression and/or other methods, and V$_{pumpout}$ is the volume of contaminated fluid pumped from the formation by the downhole tool. Equation (13) also includes OD$_{contaminated:i}$, which is the optical density of the contaminated fluid at channel i of the multichannel DFA sensor utilized to obtain measurements of fluid properties of the contaminated fluid, and $OD_{native:i}$, which is the optical density of the native fluid at channel i. Equation (14) also includes $m_{contaminated:j}$, which is the mass fraction of compositional component j of the contaminated fluid, and $m_{native:j}$, which is the mass fraction of compositional component j of the native fluid. It should be noted that the variable γ should be the same in each of Equations (11)-(14) because the linear relationship between two of GOR, density, optical density at channel i, and mass fraction of compositional component j is linearly proportional to $(V_{pumpout})^{-\gamma}$. The regression and/or other fitting method utilized to obtain the shrinkage factor b may also include fitting that utilizes exponential functions instead of power functions, among other possibilities within the scope of the present disclosure.

After fitting, extrapolation and/or other methods may be utilized to determine the fluid properties of the native fluid, including GOR ($GOR_{native}$), density ($\rho_{native}$), optical density at each channel i ($OD_{native:i}$), and mass fraction of each compositional component j ($m_{native:j}$). For example, such extrapolation may be based on the assumption that the pumpout volume (or time) approaches infinity.

In an example implementation, the apparent density ($\rho_{contaminated}$), the apparent optical density at each of i channels ($OD_{contaminated:i}$), and the mass fractions of each of j compositional components ($m_{contaminated:j}$) may be measured or otherwise obtained via DFA and then related to the apparent GOR ($GOR_{contaminated}$) by Equations (15)-(17) set forth below:

$$GOR_{contaminated}(\rho_{contaminated}) = \beta_5(\rho_{contaminated}) + \beta_6 \quad (15)$$

$$GOR_{contaminated}(OD_{contaminated:i}) = \beta_{7i}(OD_{contaminated:i}) + \beta_{8i} \quad (16)$$

$$GOR_{contaminated}(m_{contaminated:j}) = \beta_{9j}(\rho_{contaminated}) + \beta_{10j} \quad (17)$$

where $\beta_5$, $\beta_6$, $\beta_{7i}$, $\beta_{8i}$, $\beta_{9j}$, $\beta_{10j}$, are coefficients determined from DFA measurements.

For example, the DFA measurements obtained during a cleanup cycle may include, or be utilized to determine or estimate, the apparent GOR ($GOR_{contaminated}$), the apparent GOR as a function of the apparent density ($GOR_{contaminated}(\rho_{contaminated})$) from Equation (15), the apparent GOR as a function of the apparent optical density at each of i channels ($GOR_{contaminated}(OD_{contaminated:i})$) from Equation (16), and the apparent GOR as a function of the apparent mass fraction of each of j compositional components ($GOR_{contaminated}(m_{contaminated:j})$) from Equation (17), as well as the pumpout volume ($V_{pumpout}$) or time. This data may then be fit utilizing Equation (11), for example, to obtain the native GOR ($GOR_{native}$) and the fitting exponent γ. The values for fluid properties of the native fluid may then be obtained utilizing Equations (15)-(17).

Figure 16:
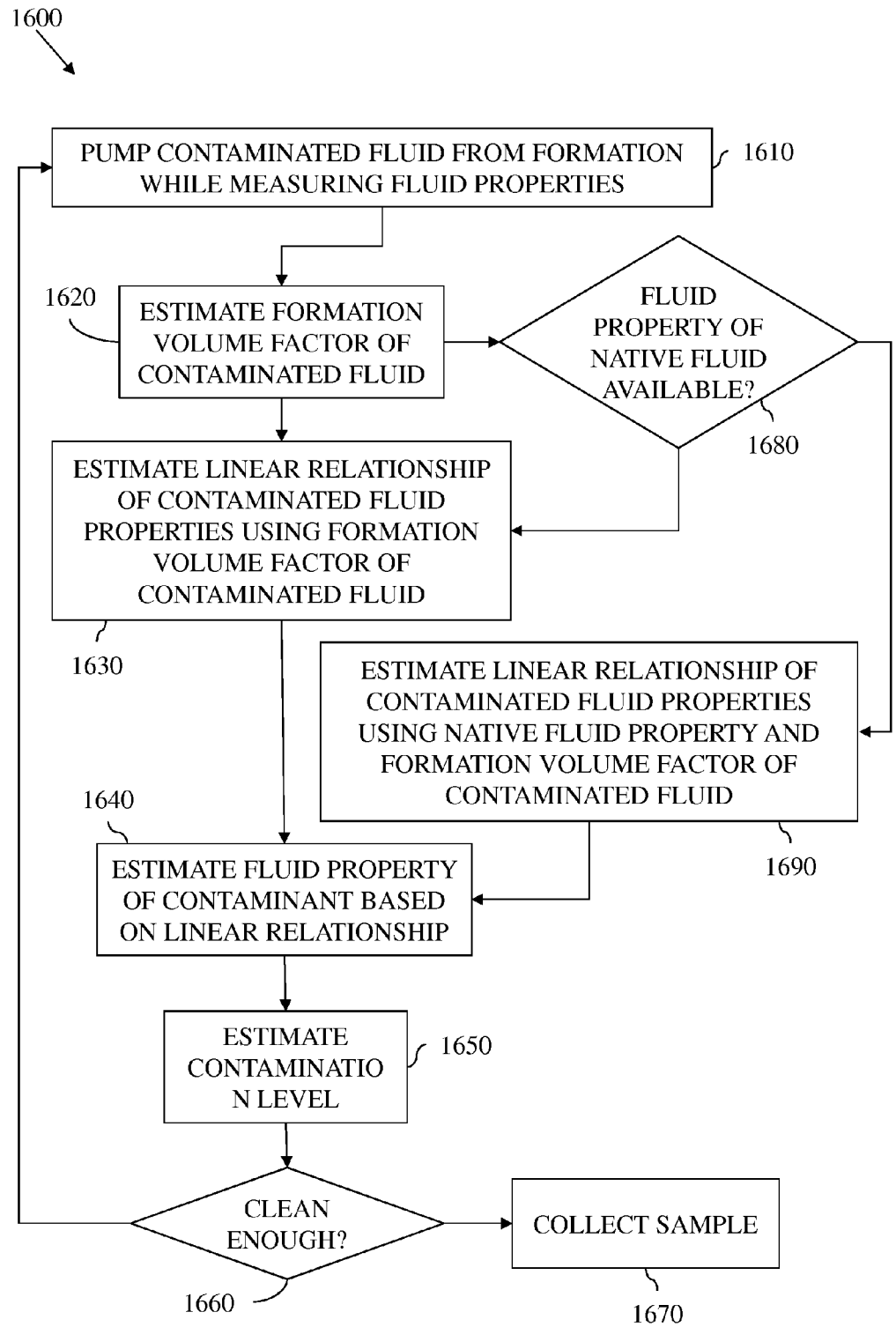
FIG. 16 is a flow-chart diagram of at least a portion of a method according to one or more aspects of the present disclosure.

FIG. 16 is a flow-chart diagram of at least a portion of a method (1600) according to one or more aspects of the present disclosure. The method (1600) may be performed via operation of at least a portion of one or more of the drilling system 10, the logging and control unit 44, the LWD modules 40, and/or the MWD modules 42 shown in FIG. 1, the wellsite surface equipment 56 and/or the spectrometer 72 shown in FIG. 2, the detector 94, detector elements 98, control/monitoring system 90, processor 100, memory 102, and/or database 104, shown in FIG. 3, and/or one or more components of the system 1700 shown in FIG. 17, among other possibilities within the scope of the present disclosure.

The method (1600) comprises pumping contaminated fluid from a subterranean formation while measuring fluid properties of the contaminated fluid (1610). The pumping may be via the pump 68 shown in FIG. 2 and/or other pumps within the scope of the present disclosure. The contaminated fluid property measurement may be via the spectrometer 72 shown in FIGS. 2 and 3 and/or other spectrometers or fluid property sensors within the scope of the present disclosure. The measured fluid property of the contaminated fluid may be one or more of density of the contaminated fluid ($\rho_{contaminated}$), optical density of the contaminated fluid ($OD_{contaminated}$), and/or GOR of the contaminated fluid ($GOR_{contaminated}$), as described above.

The method (1600) also comprises estimating (1620) a formation volume factor of the contaminated fluid ($B_{contaminated}$), as described above. Thereafter, a linear relationship of the contaminated fluid properties may be estimated (1630), wherein the linear relationship utilizes the estimated formation volume factor of the contaminated fluid ($B_{contaminated}$). For example, the linear relationship may relate the apparent density ($\rho_{contaminated}$), the apparent optical density at one or more sensor channels ($OD_{contaminated:i}$), the apparent GOR ($GOR_{contaminated}$), and/or the apparent mass fraction of one or more compositional components of the contaminated fluid ($m_{contaminated:j}$) utilizing the estimated formation volume factor of the contaminated fluid ($B_{contaminated}$), as described above. The linear relationship may include the expression $f$ in Equation (9).

The linear relationship may then be utilized to estimate (1640) a fluid property of the contaminant within the contaminated fluid (e.g., OBM filtrate). For example, the linear relationship may be extrapolated to zero-GOR to find the density and/or optical density of the OBM filtrate.

The contamination level of the contaminated fluid may then be estimated (1650) based, for example, on the estimated fluid property of the contaminant. If it is determined (1660) that the contamination level is low enough, then a sample of the contaminated fluid may be collected (1670) in the downhole tool. An acceptable contamination level may be less than about 10%, less than about 5%, or less than about 1%, depending on the particular implementation. If it is determined (1660) that the contamination level remains too high, then the downhole tool continues to pump the contamination fluid from the formation to the wellbore while measuring the fluid properties (1610).

The method (1600) may further comprise determining (1680) whether a fluid property of the native fluid in the formation is available, such as may be obtained utilizing the ongoing contaminated fluid property measurements (1610). For example, if the GOR of the native fluid ($GOR_{native}$) and/or another fluid property of the native fluid is determined (1680) to be available, then the linear relationship may be estimated (1690) utilizing the native fluid property along with the formation volume factor of the contaminated fluid. If it is determined (1680) that no additional fluid properties of the native fluid are available, then the linear relationship of the contaminated fluid properties may be estimated (1630) without utilizing additional information regarding the native fluid, such as via the expression g of Equation (10).

Figure 17:
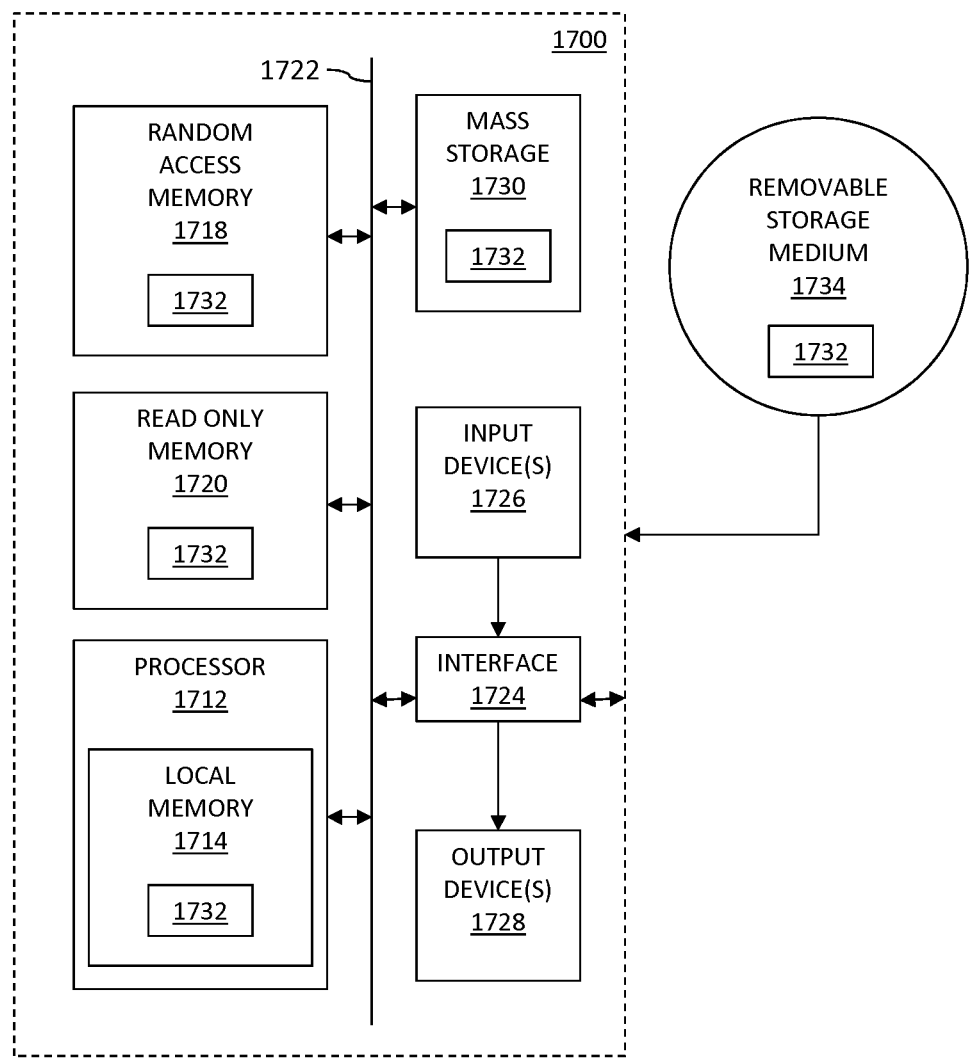
FIG. 17 is a block-diagram of at least a portion of apparatus according to one or more aspects of the present disclosure.

FIG. 17 is a block diagram of an example processing system 1700 that may execute example machine-readable instructions used to implement one or more of the methods and/or processes described herein, and/or to implement a portion of one or more of the example downhole tools described herein. The processing system 1700 may be or comprise, for example, one or more processors, controllers, special-purpose computing devices, servers, personal computers, personal digital assistant (PDA) devices, smartphones, internet appliances, and/or other types of computing devices. Moreover, while it is possible that the entirety of the system 1700 shown in FIG. 17 is implemented within the downhole tool, it is also contemplated that one or more components or functions of the system 1700 may be implemented in wellsite surface equipment, perhaps including the logging and control unit 44 and/or other wellsite surface equipment depicted in FIG. 1 and/or the wellsite surface equipment 56 shown in FIG. 2.

The system 1700 comprises a processor 1712 such as, for example, a general-purpose programmable processor. The processor 1712 includes a local memory 1714, and executes coded instructions 1732 present in the local memory 1714 and/or in another memory device. The processor 1712 may execute, among other things, machine-readable instructions to implement the methods and/or processes described herein. The processor 1712 may be, comprise, or be implemented by various types of processing units, such as one or more INTEL microprocessors, microcontrollers from the ARM and/or PICO families of microcontrollers, embedded soft/hard processors in one or more FPGAs, etc. Of course, other processors from other families are also appropriate.

The processor 1712 is in communication with a main memory including a volatile (e.g., random-access) memory 1718 and a non-volatile (e.g., read-only) memory 1720 via a bus 1722. The volatile memory 1718 may be, comprise, or be implemented by static random access memory (SRAM), synchronous dynamic random access memory (SDRAM), dynamic random access memory (DRAM), RAMBUS dynamic random access memory (RDRAM) and/or other types of random access memory devices. The non-volatile memory 1720 may be, comprise, or be implemented by flash memory and/or other types of memory devices. One or more memory controllers (not shown) may control access to the memory 1718 and/or 1720.

The processing system 1700 also includes an interface circuit 1724. The interface circuit 1724 may be, comprise, or be implemented by various types of standard interfaces, such as an Ethernet interface, a universal serial bus (USB), a third generation input/output (3GIO) interface, a wireless interface, and/or a cellular interface, among others. The interface circuit 1724 may also comprise a graphics driver card. The interface circuit 1724 may also include a communication device such as a modem or network interface card to facilitate exchange of data with external computers via a network (e.g., Ethernet connection, digital subscriber line (DSL), telephone line, coaxial cable, cellular telephone system, satellite, etc.).

One or more input devices 1726 are connected to the interface circuit 1724. The input device(s) 1726 permit a user to enter data and commands into the processor 1712. The input device(s) may be, comprise, or be implemented by, for example, a keyboard, a mouse, a touchscreen, a track-pad, a trackball, an isopoint, and/or a voice recognition system, among others.

One or more output devices 1728 are also connected to the interface circuit 1724. The output devices 1728 may be, comprise, or be implemented by, for example, display devices (e.g., a liquid crystal display or cathode ray tube display (CRT), among others), printers, and/or speakers, among others.

The processing system 1700 also includes one or more mass storage devices 1730 for storing machine-readable instructions and data. Examples of such mass storage devices 1730 include floppy disk drives, hard drive disks, compact disk drives, and digital versatile disk (DVD) drives, among others. The coded instructions 1732 may be stored in the mass storage device 1730, the volatile memory 1718, the non-volatile memory 1720, the local memory 1714, and/or on a removable storage medium, such as a CD or DVD 1734.

In view of the entirety of the present disclosure, including the figures, a person having ordinary skill in the art will readily recognize that the present disclosure introduces one or more methods comprising: operating a downhole tool within a wellbore adjacent a subterranean formation to pump contaminated fluid from the subterranean formation into the downhole tool while measuring first and second fluid properties of the contaminated fluid, wherein the contaminated fluid comprises native fluid from the subterranean formation and a contaminant, and wherein the downhole tool is in communication with surface equipment located at a wellsite surface associated with the wellbore; operating at least one of the downhole tool and the surface equipment to: estimate a formation volume factor of the contaminated fluid based on at least one of the first and second fluid properties of the contaminated fluid; estimate a linear relationship between the first fluid property and a function comprising: the second fluid property; and the estimated formation volume factor of the contaminated fluid; and estimate a fluid property of the contaminant based on the estimated linear relationship. Such method(s) may further comprise estimating a contamination level of the contaminated fluid based at least on: the estimated formation volume factor of the contaminated fluid; the estimated fluid property of the contaminant; and at least one of the first and second fluid properties of the contaminated fluid. Such method(s) may further comprise operating at least one of the downhole tool and the surface equipment to estimate a fluid property of the native fluid based on at least one of the first and second fluid properties of the contaminated fluid, wherein the function further comprises the estimated fluid property of the native fluid.

In such method(s), the contaminant may comprise OBM filtrate that has passed from the wellbore into the subterranean formation. The contaminated fluid may have a GOR greater than about 700 scf/bbl.

The first fluid property of the contaminated fluid may be density, and the second fluid property of the contaminated fluid may be GOR. In a similar implementation, the first fluid property of the contaminated fluid may be optical density, and the second fluid property of the contaminated fluid may be GOR. In other implementations, the first fluid property of the contaminated fluid may not be density or optical density, yet the second fluid property of the contaminated fluid may nonetheless be GOR. The first fluid property of the contaminated fluid may be substantially not proportionally linear to the second fluid property of the contaminated fluid.

The first fluid property may be density of the contaminated fluid ($\rho_{contaminated}$), the second fluid property may be GOR of the contaminated fluid ($GOR_{contaminated}$), and the linear relationship may be given by $\rho_{contaminated} = b \, (GOR_{contaminated})$, where b is the inverse of the estimated formation volume factor of the contaminated fluid.

Methods of the present disclosure may further comprise operating at least one of the downhole tool and the surface equipment to estimate the GOR of the native fluid ($GOR_{native}$) based on at least one of the first and second fluid properties of the contaminated fluid, wherein the first fluid property may be density of the contaminated fluid ($\rho_{contaminated}$), the second fluid property may be GOR of the contaminated fluid ($GOR_{contaminated}$), and the linear relationship may be given by $\rho_{contaminated} = GOR_{native} - b$ ($GOR_{native} - GOR_{contaminated}$), where b is the inverse of the estimated formation volume factor of the contaminated fluid.

The present disclosure also introduces one or more systems comprising: surface equipment located at a wellsite surface associated with a wellbore extending into a subterranean formation; a downhole tool operable within the wellbore to: communicate with the surface equipment; pump contaminated fluid from the subterranean formation into the downhole tool, wherein the contaminated fluid comprises native fluid from the subterranean formation and a contaminant; and measure first and second fluid properties of the contaminated fluid; and at least one processor comprised by at least one of the surface equipment and the downhole tool, wherein the at least one processor is operable to: estimate a formation volume factor of the contaminated fluid based on at least one of the first and second fluid properties of the contaminated fluid; estimate a linear relationship between the first fluid property and a function comprising: the second fluid property; and the estimated formation volume factor of the contaminated fluid; and estimate a fluid property of the contaminant based on the estimated linear relationship.

In such system(s), the at least one processor may be further operable to estimate a contamination level of the contaminated fluid based at least on: the estimated formation volume factor of the contaminated fluid; the estimated fluid property of the contaminant; and at least one of the first and second fluid properties of the contaminated fluid.

In such system(s), the at least one processor may be further operable to estimate a fluid property of the contaminated fluid based on at least one of the first and second fluid properties of the contaminated fluid, and the function may further comprise the estimated fluid property of the native fluid.

In such system(s), the contaminant may comprise oil-based mud (OBM) filtrate that has passed from the wellbore into the subterranean formation. The contaminated fluid may have a GOR greater than about 700 scf/bbl.

The first fluid property of the contaminated fluid may be the density or optical density and the second fluid property of the contaminated fluid may be the GOR of the contaminated fluid.

The downhole tool may comprise an optical spectrometer operable to measure an optical characteristic of the contaminated fluid over a plurality of wavelengths to generate optical spectra data indicative of at least one of the first and second fluid properties of the contaminated fluid.

The present disclosure also introduces one or more methods comprising: operating a downhole tool within a wellbore adjacent a subterranean formation to pump contaminated fluid from the subterranean formation into the downhole tool while measuring first and second fluid properties of the contaminated fluid, wherein the contaminated fluid comprises native fluid from the subterranean formation and a contaminant, and wherein the downhole tool is in communication with surface equipment located at a wellsite surface associated with the wellbore; operating at least one of the downhole tool and the surface equipment to estimate a formation volume factor of the contaminated fluid based on at least one of the first and second fluid properties of the contaminated fluid; operating at least one of the downhole tool and the surface equipment to determine whether a fluid property of the native fluid can be estimated based on at least one of the first and second fluid properties of the contaminated fluid; if the fluid property of the native fluid can be estimated based on at least one of the first and second fluid properties of the contaminated fluid, operating at least one of the downhole tool and the surface equipment to: estimate the fluid property of the native fluid based on at least one of the first and second fluid properties of the contaminated fluid; and estimate a linear relationship between the first fluid property and a function comprising: the second fluid property; the estimated formation volume factor of the contaminated fluid; and the estimated fluid property of the native fluid; and if the fluid property of the native fluid cannot be estimated based on at least one of the first and second fluid properties of the contaminated fluid, operating at least one of the downhole tool and the surface equipment to: estimate a linear relationship between the first fluid property and a function comprising: the second fluid property; and the estimated formation volume factor of the contaminated fluid. Such method(s) may further comprise operating at least one of the downhole tool and the equipment to estimate a contamination level of the contaminated fluid based at least on: the estimated formation volume factor of the contaminated fluid; the estimated fluid property of the contaminant; and at least one of the first and second fluid properties of the contaminated fluid.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same purposes and/or achieving the same advantages of the embodiments introduced herein. A person having ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. A method, comprising:
   operating a downhole tool within a wellbore adjacent a subterranean formation to pump contaminated fluid from the subterranean formation into the downhole tool while measuring first and second fluid properties of the contaminated fluid, wherein the contaminated fluid comprises native fluid from the subterranean formation and a contaminant, and wherein the downhole tool is in communication with surface equipment located at a wellsite surface associated with the wellbore;
   operating at least one of the downhole tool and the surface equipment to:
   estimate a formation volume factor of the contaminated fluid based on at least one of the first and second fluid properties of the contaminated fluid;
   estimate a linear relationship between the first fluid property and a function comprising:
   the second fluid property; and
   the estimated formation volume factor of the contaminated fluid; and
   estimate a fluid property of the contaminant based on the estimated linear relationship.

2. The method of claim 1 further comprising estimating a contamination level of the contaminated fluid based at least on:
   the estimated formation volume factor of the contaminated fluid;

the estimated fluid property of the contaminant; and
at least one of the first and second fluid properties of the contaminated fluid.

3. The method of claim 1 further comprising operating at least one of the downhole tool and the surface equipment to estimate a fluid property of the native fluid based on at least one of the first and second fluid properties of the contaminated fluid, wherein the function further comprises the estimated fluid property of the native fluid.

4. The method of claim 1 wherein the contaminant comprises oil-based mud (OBM) filtrate that has passed from the wellbore into the subterranean formation.

5. The method of claim 4 wherein the contaminated fluid has a gas/oil ratio (GOR) greater than about 700 scf/bbl.

6. The method of claim 1 wherein the first fluid property of the contaminated fluid is density of the contaminated fluid.

7. The method of claim 6 wherein the second fluid property of the contaminated fluid is gas/oil ratio (GOR) of the contaminated fluid.

8. The method of claim 1 wherein the first fluid property of the contaminated fluid is optical density of the contaminated fluid.

9. The method of claim 8 wherein the second fluid property of the contaminated fluid is gas/oil ratio (GOR) of the contaminated fluid.

10. The method of claim 1 wherein the second fluid property of the contaminated fluid is gas/oil ratio (GOR) of the contaminated fluid.

11. The method of claim 1 wherein the first fluid property of the contaminated fluid is substantially not proportionally linear to the second fluid property of the contaminated fluid.

12. The method of claim 1 wherein the first fluid property is density of the contaminated fluid ($\rho_{contaminated}$), the second fluid property is gas/oil ratio of the contaminated fluid ($GOR_{contaminated}$), and the linear relationship is given by:

$$\rho_{contaminated} = b(GOR_{contaminated})$$

where b is the inverse of the estimated formation volume factor of the contaminated fluid.

13. The method of claim 1 further comprising operating at least one of the downhole tool and the surface equipment to estimate gas/oil ratio of the native fluid ($GOR_{native}$) based on at least one of the first and second fluid properties of the contaminated fluid, wherein the first fluid property is density of the contaminated fluid ($\rho_{contaminated}$), the second fluid property is gas/oil ratio of the contaminated fluid ($GOR_{contaminated}$), and the linear relationship is given by:

$$\rho_{contaminated} = GOR_{native} - b(GOR_{native} - GOR_{contaminated})$$

where b is the inverse of the estimated formation volume factor of the contaminated fluid.

14. A system, comprising:
surface equipment located at a wellsite surface associated with a wellbore extending into a subterranean formation;
a downhole tool operable within the wellbore to:
communicate with the surface equipment;
pump contaminated fluid from the subterranean formation into the downhole tool, wherein the contaminated fluid comprises native fluid from the subterranean formation and a contaminant; and
measure first and second fluid properties of the contaminated fluid; and
at least one processor comprised by at least one of the surface equipment and the downhole tool, wherein the at least one processor is operable to:
estimate a formation volume factor of the contaminated fluid based on at least one of the first and second fluid properties of the contaminated fluid;
estimate a linear relationship between the first fluid property and a function comprising:
the second fluid property; and
the estimated formation volume factor of the contaminated fluid; and
estimate a fluid property of the contaminant based on the estimated linear relationship.

15. The system of claim 14 wherein the at least one processor is further operable to estimate a contamination level of the contaminated fluid based at least on:
the estimated formation volume factor of the contaminated fluid;
the estimated fluid property of the contaminant; and
at least one of the first and second fluid properties of the contaminated fluid.

16. The system of claim 14 wherein the at least one processor is further operable to estimate a fluid property of the native fluid based on at least one of the first and second fluid properties of the contaminated fluid, and wherein the function further comprises the estimated fluid property of the native fluid.

17. The method of claim 1 wherein the first fluid property of the contaminated fluid is density or optical density of the contaminated fluid and the second fluid property of the contaminated fluid is gas/oil ratio (GOR) of the contaminated fluid.

18. The system of claim 14 wherein the downhole tool comprises an optical spectrometer operable to measure an optical characteristic of the contaminated fluid over a plurality of wavelengths to generate optical spectra data indicative of at least one of the first and second fluid properties of the contaminated fluid.

19. A method, comprising:
operating a downhole tool within a wellbore adjacent a subterranean formation to pump contaminated fluid from the subterranean formation into the downhole tool while measuring first and second fluid properties of the contaminated fluid, wherein the contaminated fluid comprises native fluid from the subterranean formation and a contaminant, and wherein the downhole tool is in communication with surface equipment located at a wellsite surface associated with the wellbore;
operating at least one of the downhole tool and the surface equipment to estimate a formation volume factor of the contaminated fluid based on at least one of the first and second fluid properties of the contaminated fluid;
operating at least one of the downhole tool and the surface equipment to determine whether a fluid property of the native fluid can be estimated based on at least one of the first and second fluid properties of the contaminated fluid;
if the fluid property of the native fluid can be estimated based on at least one of the first and second fluid properties of the contaminated fluid, operating at least one of the downhole tool and the surface equipment to:
estimate the fluid property of the native fluid based on at least one of the first and second fluid properties of the contaminated fluid; and
estimate a linear relationship between the first fluid property and a function comprising:
the second fluid property;
the estimated formation volume factor of the contaminated fluid; and
the estimated fluid property of the native fluid; and if the fluid property of the native fluid cannot be estimated based on at least one of the first and second fluid properties of the contaminated fluid, operating at least one of the downhole tool and the surface equipment to:
  estimate a linear relationship between the first fluid property and a function comprising:
    the second fluid property; and
    the estimated formation volume factor of the contaminated fluid.

20. The method of claim 19 further comprising operating at least one of the downhole tool and the equipment to estimate a contamination level of the contaminated fluid based at least on:
  the estimated formation volume factor of the contaminated fluid;
  the estimated fluid property of the contaminant; and
  at least one of the first and second fluid properties of the contaminated fluid.

* * * * *